United States Patent [19]

Cebalo et al.

[11] 4,290,798

[45] Sep. 22, 1981

[54] HERBICIDAL COMPOUND AND METHOD OF USE

[75] Inventors: Tony Cebalo, Indianapolis, Ind.; Robert A. Walde, Allison Park, Pa.

[73] Assignee: Air Products and Chemicals, Inc., Allentown, Pa.

[21] Appl. No.: 964,757

[22] Filed: Nov. 29, 1978

Related U.S. Application Data

[60] Continuation-in-part of Ser. No. 783,521, Apr. 1, 1977, abandoned, which is a division of Ser. No. 601,739, Aug. 4, 1975, abandoned, which is a continuation of Ser. No. 453,630, Mar. 22, 1974, abandoned, which is a continuation-in-part of Ser. No. 280,605, Aug. 14, 1972, abandoned.

[51] Int. Cl.³ .................... A01N 47/36; C07D 285/12
[52] U.S. Cl. ........................................ 71/90; 548/141
[58] Field of Search .................. 260/306.8 D; 71/90; 548/141

[56] References Cited

U.S. PATENT DOCUMENTS

| | | | |
|---|---|---|---|
| 3,803,164 | 4/1974 | Tao | 260/306.8 D |
| 3,880,873 | 4/1975 | Doyle et al. | 260/306.8 D |
| 3,937,715 | 2/1976 | Röchling et al. | 260/306.8 D |
| 4,086,077 | 4/1978 | Doyle | 548/141 |
| 4,097,264 | 6/1978 | Kirkpatrick et al. | 260/306.8 D |

FOREIGN PATENT DOCUMENTS

| | | | |
|---|---|---|---|
| 765930 | 9/1971 | Belgium | 71/90 |
| 1195672 | 6/1970 | United Kingdom | 260/306.8 D |
| 1266172 | 3/1972 | United Kingdom | 260/306.8 D |
| 1276925 | 6/1972 | United Kingdom | 260/306.8 D |

OTHER PUBLICATIONS

Sato, Chem. Abstracts, vol. 72, Abstract No. 43685f, (1970).
Kubo et al., J. Agr. Food Chem., vol. 18, pp. 60-65, (1970).

*Primary Examiner*—Alton D. Rollins
*Attorney, Agent, or Firm*—Dwight E. Morrison; Arthur R. Whale

[57] ABSTRACT

This invention relates to a novel substituted thiadiazole, identified as 1-[5-(2-chloro-1,1-dimethylethyl)-1,3,4-thiadiazol-2-yl]-1,3-dimethylurea, to its use in a novel method for the control of unwanted vegetation, and to a novel herbicidal composition employing the substituted thiadiazole as the herbicidally-active ingredient.

3 Claims, No Drawings

HERBICIDAL COMPOUND AND METHOD OF USE

CROSS-REFERENCE

This application is a continuation-in-part of application Ser. No 783,521, filed Apr. 1, 1977, now abandoned which is a division of application Ser. No. 601,739, filed Aug. 4, 1975, now abandoned, which was a continuation of then copending application Ser. No. 453,630, filed Mar. 22, 1974, now abandoned, which was a continuation-in-part of then copending application Ser. No. 280,605, filed Aug. 14, 1972, now abandoned.

BACKGROUND OF THE INVENTION

1. Field of the Invention

This invention relates to a novel substituted thiadiazole which possesses herbicidal activity, in particular, activity as a selective herbicide in sugarcane and citrus. The invention also relates to a method for controlling unwanted vegetation using the compound, and to herbicidal compositions containing the compound.

2. Description of the Prior Art

While the prior art refers to many thiadiazoles and derivatives thereof, none of the prior art teaches the unexpected herbicidal selectivity against sugarcane and citrus demonstrated by the compound disclosed and claimed herein.

In the prior art, British Pat. No. 1,195,672 (published June 17, 1970), discloses and claims thiadiazolylureas, including compounds having a haloalkyl substituent at the 5-position of the thiadiazole ring. The compounds are alleged to be active both as pre- and postemergent herbicides.

Also in the prior art is British Pat. No. 1,266,172 (published Mar. 8, 1972), which discloses and claims thiadiazolylureas having an acyclic hydrocarbon radical or a halogenated derivative thereof at the 5-position of the thiadiazole ring. These disclosed thiadiazolylureas are alleged to have utility as agricultural chemicals, that is, they are active as herbicides, plant fungicides, insecticides, and/or acaricides. When used as herbicides, the compounds are alleged to be active when applied either preemergence or postemergence. Some of the compounds may be applied to weeds or crops for defoliation or dessication, and others are suitable for use in herbicidal soil sterilant applications.

Yet another prior art reference is British Patent Application No. 1,276,925 (published June 7, 1972), which is directed to 1,3,4-thiadiazolylureas substituted in the 5-position of the thiadiazole ring with haloalkyl or trifluoroalkoxyalkyl groups, to a process for producing the compounds, and to their use as herbicides. The compounds are alleged to exhibit a good selectivity when applied either pre- or postemergence in cotton, and in cereals such as wheat and oats.

Still another prior art reference is U.S. Pat. No. 3,937,715 (Feb. 10, 1976), which reference is directed to 2-(tetrahaloethyl)-5-amino-1,3,4-thia- or oxadiazoles and their salts, alleged to be active as plant growth regulators and herbicides, and alleged to be especially valuable for dwarfing barley. The compounds of the reference bear a 1,1-difluoro-2,3-dichloroethyl substituent at the 5-position of the thiadiazole ring.

Also in the prior art is U.S. Pat. No. 4,097,264 (June 27, 1978), which discloses thiadiazolylureas substituted in the 5-position with a monochloro or di-chloro-t-butyl moiety. The compounds are alleged to be useful in herbicidal compositions and methods for controlling unwanted vegetation by pre- or postemergent application.

SUMMARY OF THE INVENTION

The present invention relates to a novel substituted thiadiazole which possesses herbicidal activity, in particular as a selective herbicide in sugarcane and citrus, as well as to novel herbicidal compositions containing the compound, and to a novel method of controlling unwanted vegetation.

DESCRIPTION OF THE PREFERRED EMBODIMENT

This invention relates in one embodiment to the novel compound 1-[5-(2-chloro-1,1-dimethylethyl)-1,3,4-thiadiazol-2-yl]-1,3-dimethylurea, of the formula

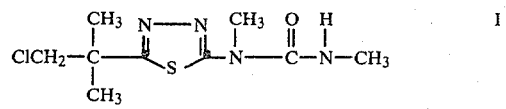

This invention relates in another embodiment to herbicidal compositions containing the compound. In another embodiment, this invention relates to a novel method of controlling undesired vegetation which comprises applying to the locus of the undesired vegetation a herbicidally-effective amount of compound (I).

The novel compound of this invention is active in the greenhouse as a pre- or a post-emergent herbicide at application rates ranging from about 0.28 to about 2.24 kilogram per hectare (kg./ha). As is well understood by those of ordinary skill in the herbicide art, somewhat greater application rates are necessary in the field, for example from about 0.75 to about 6.72 kg./ha., suitably from about 0.84 to about 4.48 kg./ha.

The herbicidal compound shows unexpected selectivity and safety on citrus trees. Thus, the novel compound is useful for the control of unwanted vegetation in citrus groves when applied at the rate of from about 0.75 to about 6.72 kg./ha., suitably from about 0.84 to about 4.48 kg./ha.

In addition to the above-described selectivity and safety to citrus trees, the novel compound of this invention also shows itself to be selective in its herbicidal action on sugarcane. The compound is therefore useful as a selective herbicide in the cultivation of sugarcane, when applied at the rate of from about 1.12 to about 4.48 kg./ha.

The present novel compound is prepared using starting materials and procedures known to those of ordinary skill in the art.

The intermediate 2-(substituted amino)-5-substituted-1,3,4-thiadiazole used to synthesize the novel compound of this invention is prepared by the method disclosed in U.S. Pat. No. 3,669,982 (June 13, 1972), which disclosure is hereby incorporated herein and made a part of this application.

According to that method, 5-(2-chloro-1,1-dimethylethyl)-2-methylamino-1,3,4-thiadiazole is prepared by allowing a suspension of α-chloro-α,α-dimethylpropionic acid (also called β-chloropivalic acid) and 4-methylthiosemicarbazide in dioxane to react with phosphorus oxychloride.

The final product, the novel thiadiazol-2-ylurea, is prepared by a synthesis known to those of ordinary skill in the art.

Thus, the 5-(2-chloro-1,1-dimethylethyl)-2-methylamino-1,3,4-thiadiazole is allowed to react with methyl isocyanate in a suitable solvent at a temperature and for a time sufficient to bring about substantially complete reaction. Suitable inert solvents include ethyl acetate, benzene, toluene, or the like. A suitable reaction temperature is the reflux temperature of the reaction mixture. The reaction time may vary, but usually from about 2.5 to about 3 or 4 hours is suitable.

The preparation of the intermediate 2-substituted amino-5-substituted-1,3,4-thiadiazole compound is described in the Preparation, which follows.

PREPARATION 1

5-(2-Chloro-1,1-dimethylethyl)-2-methylamino-1,3,4-thiadiazole

A mixture of 1410 g. (10.0 moles) of β-chloropivalic acid, 1050 g. (10.0 moles) of 4-methylthiosemicarbazide, and 6.2 l. of dioxane was placed in a 22 l. round-bottom 5-neck flask equipped with a mechanical stirrer, two condensers with calcium chloride drying tubes, a thermometer, a dropping funnel, and a heating mantle. The mixture was heated to a temperature of about 90° C., and the addition of 1690 g. (11.0 moles) of phosphorus oxychloride at a slow rate was begun, the rate of addition being adjusted to maintain the temperature of the reaction mixture at about 95°–97° C. When the addition was complete, the temperature of the reaction mixture was adjusted to about 90° C., and the mixture maintained at that temperature overnight, with continued stirring.

The reaction mixture became very thick and gummy and difficult to stir. It was cooled to about 50°–70° C., and the dioxane decanted, leaving a residue. Twelve liters of hot (50°–55° C.) water was then added, with stirring, to dissolve the residue. The mixture was filtered via a filter stick. The filtrate was transferred to a 40 l. pot with about 10 l. of ice. The mixture was stirred, kept cold with ice, and made basic by the addition of 28% aqueous ammonia. A solid material separated, was filtered off, washed with water, and air dried. The solid thus obtained weighed 1798 g., had a melting point of about 79°–80° C., and was identified by its NMR spectrum as 5-(2-chloro-1,1-dimethylethyl)-2-methylamino-1,3,4-thiadiazole.

Using the intermediate compound synthesized as described above, the final novel product useful in the novel herbicidal method and the novel herbicidal composition of this invention was prepared according to the following Example.

EXAMPLE 1

1-[5-(2-Chloro-1,1-dimethylethyl)-1,3,4-thiadiazol-2-yl]-1,3-dimethylurea

A mixture of 10,500 g. (51.1 moles) of 5-(2-chloro-1,1-dimethylethyl)-2-methylamino-1,3,4-thiadiazole and 50 l. of toluene was placed under a dry nitrogen atmosphere. in a 50 gallon, glass-lined still, and azeotroped until dry.

The mixture, still under dry nitrogen atmosphere, was maintained at a temperature of about 36°–38° C., while 3,203 g. (56.2 moles) of methyl isocyanate was slowly added with stirring over a period of about 1 hour. The reaction was somewhat exothermic, but was readily controlled by circulating cold water in the cooling jacket surrounding the still. When the addition was complete, stirring was continued, and the temperature of the reaction mixture was increased to about 70° C., and maintained at this temperature for about 2.5 hours.

At the end of this time, the reaction mixture was cooled to about 25° C., and 1500 ml. of 28% aqueous ammonia was added to destroy any unreacted methyl isocyanate. The mixture was then cooled to about 0° C., and held at that temperature for about 1 hour. The solid material which separated was filtered off and washed with cold water, and air dried at about 75° C. The product weighed 11,229 g. (84% yield), had a melting point of about 151°–153° C., and was identified by NMR spectrum as 1-[5-(2-chloro-1,1-dimethylethyl)-1,3,4-thiadiazol-2-yl]-1,3-dimethylurea.

To be utilized in the novel herbicidal method of the present invention, the above-described compound may be formulated in novel compositions comprising the above-described compound as the active ingredient and a solid or liquid inert carrier. Such novel compositions are useful and convenient for preparing the mixture desired for application to the locus of desired vegetation control. It is recognized that the particular type and concentration of formulation, as well as the mode of application of the active ingredient, may govern its biological activity in a given application.

This active compound may be formulated as a simple solution in an appropriate solvent in which it is completely soluble at the desired concentration. Such solvent systems include alcohols, acetone, aqueous alcohol and aqueous acetone, xylene, heavy aromatic naphthas, and other organic solvents. These simple solutions may be further modified by the addition of various surfactants, emulsifying or dispersing agents, colorants, odorants, antifoaming agents, or other herbicides or herbicidal oils which supplement or synergize the activity of the herbicide of the invention.

The compound useful in the herbicidal method of the present invention may also be formulated in various types of formulations commonly recognized by those skilled in the art of agricultural or industrial chemicals. These formulations include, for example, compositions containing the active ingredient as granules of relatively large particle size, as powder dusts, as wettable powders, as emulsifiable concentrates, or as a constituent part of any other known type of formulation commonly utilized by those skilled in the art. Such formulations include the adjuvants and carriers normally employed for facilitating the dispersion of an active ingredient for agricultural and industrial applications of phytotoxicants. These formulations may contain as little as 0.1% or as much as 90% by weight of the active ingredient.

Dust formulations are prepared by mixing the active ingredient with finely divided solids which act as dispersants and carriers for the phytotoxicant in applying it to the locus of desired vegetation control. Typical solids which may be utilized in preparing dust formulations of the active ingredient useful in the invention include talc, kieselguhr, finely divided clay, fuller's earth, or other common organic or inorganic solids. Solids utilized in preparing dust formulations of the active ingredient normally have a particle size of 50 microns or less. The active ingredient of these dust formulations is present commonly in from as little as 0.5% to as much as 90% or more by weight of the composition.

Granular formulations of the active ingredient are prepared by impregnating or adsorbing the toxicant on or into relatively coarse particles of inert solids such as sand, attapulgite clay, gypsum, corncobs, vermiculite, or other inorganic or organic solids. The active ingredient of these granular formulations is commonly present in from 0.1% to as much as 90% or more by weight of the composition.

The compound useful in the novel herbicidal method of this invention may also be formulated as a wettable powder. Wettable powder formulations are solid compositions of matter wherein the active ingredient is absorbed or adsorbed in or on a sorptive carrier such as finely divided clay, talc, gypsum, lime, wood flour, fuller's earth, kieselguhr or the like. These formulations preferably are made to contain 0.5% to 90% of active ingredient. These wettable powder formulations commonly contain a small amount of a wetting, dispersing, or emulsifying agent to facilitate dispersion in water or other liquid carrier utilized to distribute the phytotoxicant to the locus of desired vegetation control. Suitable wetting and/or dispersing agents included condensed aryl sulfonic acids and sodium salts thereof, sodium lignosulfonate, sulfonate-oxide condensate blends, alkyl aryl polyether alcohols, sulfonated nonionic blends, anionic wetting agents, and the like. Suitable emulsifying agents can be of the nonionic or ionic types, or blends thereof, and include condensation products of alkylene oxides with phenols and organic acids, polyoxyethylene derivatives of sorbitan esters, complex ether-alcohols, ionics of the aralkyl sulfonate type, and the like.

The compound used in this herbicidal method may also be formulated as an emulsifiable concentrate. Emulsifiable concentrate formulations are homogenous, liquid or paste compositions containing the active ingredient, which compositions will disperse in water or other liquid carrier to facilitate application of the phytotoxicant to the locus of desired vegetation control. Such emulsifiable concentrate formulations of the active ingredient may contain only the active ingredient with a liquid or solid emulsifying agent, or may contain other relatively nonvolatile organic solvents such as isophorone, dioxane, heavy aromatic naphthas, xylene, or dimethylformamide. Emulsifying agents suitable for use in preparing these emulsifiable concentrate compositions are described in the immediately previous paragraph. The active ingredient in such a formulation commonly comprises from about 1% to about 70% by weight of the phytotoxicant composition.

The compound usable in the herbicidal method of this invention may also be formulated in both pellet and tablet form.

The pellets are produced by combining the solid ingredients of the formulation in a suitable mixer, such as a ribbon blender, or the like. The active compound is placed in the blender together with one or more of a number of appropriate additives or excipients, such as clay, or a similar inert ingredient, a wetting agent, a dispersant, a lubricant, a binder, or the like, and the whole mixed with water. The mixture thus formed is transferred to the pellet mill for further processing. The size of the pellets is determined by the diameter of the die of the mill and the setting of the knives. After formation of the pellets, they are dried and screened to remove fines before packaging.

The tablet formulations are prepared by methods well-known to those skilled in the art of tablet preparation and who are knowledgeable in the field of agricultural chemicals. Thus, the active ingredient is compounded with a suitable binder, other excipients and extenders, lubricants, and the like, the mixture granulated and compressed into tablets.

The following experimental procedure was used to demonstrate the pre- and postemergent herbicidal activity of the novel compound of Example 1 of this application. Since there is only the one test compound in each trail, the compound is simply identified in column 1 of each table of results by the numeral "1".

TRIAL 1

A soil was prepared consisting of one part masonry sand and one part shredded top soil belended together and then autoclaved. Plantings were made in galvanized metal flats which measure 31.5 cm. long, 21.5 cm. wide, and 8 cm. deep, with holes and grooves in the bottom for drainage. Each flat was filled two-thirds full with autoclaved soil and the soil was leveled and tamped. All the seeds were planted in rows perpendicular to the long axis of the flat. Both pre- and postemergence applications were tested in flats by planting the following seeds: corn (*Zea mays*), sorghum (*Sorghum vulgare*), soybean (*Glycine max*), foxtail millet (*Setaria italica*), browntop panicum (*Panicum fasciculatum*), velvetleaf (*Abutilon theophrasti*), and morningglory (*Ipomoea purpurea*). The preemergence flats were planted on the day of treatment, while the postemergence flats were planted 10 to 13 days prior to treatment and placed in a growth chamber until the day of treatment. In the growth chamber, flats received 12 to 18 hours of light per day and were subject to temperatures of 75° to 85° F.

The compound studied in this test was applied at rates of 0.28, 0.56, 1.12, and 2.24 kg./ha., pre- and postemergent. The formulation for an application rate of 2.24 kg./ha. was accomplished by dissolving 60 mg. of the test compound in about 5 ml. of a solvent containing acetone and ethyl alcohol in a 1:1 ratio, together with a small amount of Toximul R and S. The solution was then diluted with deionized water to 50 ml., to provide the formulation for the application rate of 2.24 kg./ha. This formulation was then serially diluted with deionized water containing 1,000 ppm. of Toximul R and S to give the other desired application rates. Toximul R and Toximul S are sulfonate/non-ionic blends which are products of Stepan Chemical Company, Northfield, Illinois.

The herbicidal compositions were applied to each flat with a modified DeVilbiss atomizer hooked to an air source. Twelve and one-half ml. of the composition under test was applied to each flat. One pre- and one postemergent flat were treated at each rate. The preemergent flats were treated by surface application of the test solutions the day the seeds were planted. The postemergent flats were treated by an over-the-top spray about 12 days after planting for all rates except the 2.24 kg./ha. rate. The over-the-top spray at the 2.24 kg/ha. rate was applied 8 days post-planting.

The herbicidal effects of the compound were evaluated 15 days after treatment (DAT). The degree of plant injury is based on a 0 to 10 scale wherein 0 equals no injury and 10 equals 100% kill.

Table 1, which follows, sets forth the results of the pre- and postemergent testing of the compound of this application. In the table, column 2 gives the rate in terms of kg./ha. at which the compound was applied to the test flat; and columns 3 through 16, the injury rating for particular plant species.

The test plants are identified by letters of the alphabet, as set forth hereinbelow:

A—Corn
B—Morningglory
C—Browntop panicum
D—Velvetleaf
E—Foxtail millet
F—Sorghum
G—Soybean replicates of each test, there were included control plots to which no test compound was applied.

The test compound was applied 54 days following the planting of the orange trees. Beginning 42 days after treatment (DAT), the treated trees and controls were observed periodically for evidence of any possible injury caused by the test compounds. What injury was observed was characterized as dwarfed chlorotic leaves. The results of the observations as to possible

TABLE 1

PLANT INJURY RATINGS 15 DAT

| Compound | Appln. Rate kg./ha. | Pre-Emergence | | | | | | | Post-Emergence | | | | | | |
|---|---|---|---|---|---|---|---|---|---|---|---|---|---|---|---|
| | | A | B | C | D | E | F | G | A | B | C | D | E | F | G |
| 1 | 0.28 | 1 | 8 | 8.5 | 10 | 7.5 | 6 | 4 | 0 | 8 | 6 | 10 | 6 | 4 | 9.5 |
| | 0.56 | 3 | 10 | 9.9 | 10 | 9 | 7 | 8.5 | 6 | 9.5 | 9 | 10 | 9.5 | 6 | 10 |
| | 1.12 | 7 | 10 | 10 | 10 | 9.9 | 9.9 | 9.8 | 6 | 9.8 | 9.8 | 10 | 9.8 | 7.5 | 10 |
| | 2.24 | 9.8 | 10 | 10 | 10 | 10 | 10 | 9.8 | 10 | 10 | 10 | 10 | 10 | 10 | 10 |
| Control | | 0 | 0 | 0 | 0 | 0 | 0 | 0 | 0 | 0 | 0 | 0 | 0 | 0 | 0 |

The broad spectrum of the herbicidal activity of the instant compound has been demonstrated by the test results set forth hereinabove.

In order to demonstrate the selective herbicidal activity of the compound when applied to unwanted vegetation in the presence of citrus trees, and the safety of the compound to citrus trees, additional testing was conducted. Both greenhouse trials and field trials were conducted. Since field trials more closely approximate actual use of the novel compound of this invention, the field trials are described herein.

crop injury are set forth in Table 2, which follows. The crop injury was recorded as percent crop injury, the rating scale being as follows:

0% = no injury
10-30% = slight injury
40-60% = moderate injury
70-90% = severe injury
100% = death In the table, column 2 gives the application rate in kg./ha.; and columns 3 through 9, inclusive, the percent crop injury on the designated days after treatment (DAT).

TABLE 2

PERCENT CROP INJURY

| Compound | kg./ha. | 42 DAT | 85 DAT | 142 DAT | 175 DAT | 215 DAT | 254 DAT | 315 DAT |
|---|---|---|---|---|---|---|---|---|
| 1 | 1.12 | 13 | 0 | 0 | 0 | 0 | 0 | 0 |
| | 2.24 | 3 | 10 | 3 | 7 | 0 | 0 | 0 |
| | 4.48 | 0 | 20 | 0 | 7 | 3 | 0 | 0 |
| Control | | 0 | 0 | 0 | 0 | 0 | 0 | 0 |

TRIAL 2

This trial was conducted using sweet orange trees, variety Valencia. The trees were about 2 years old and about 90 cm. tall. The trees were planted one tree per plot, each plot measuring about 0.9×0.9 meters. The plots were in rows 2.95 meters wide. The oil was sandy, contained no clods, and had an organic content of about 1.2%, as shown by testing. The land was flat. The soil surface was moist and the soil moisture was intermediate. The randomized block experimental design was followed, using three replicates per test.

The test compound was formulated as a 25% wettable powder (25% WP). The formulation was then diluted with water to obtain the proper concentration of test material, and applied using a $CO_2$ backpack sprayer. The spray was directed to the base of the crop, avoiding the foliage of the crop. The band width sprayed was about 0.46 meters and the test material was applied at the rate of about 374 l./ha. In addition to the three The efficacy of Compound 1 in controlling undesirable weeds and grasses around the orange trees was also observed, beginning about 22 days after treatment (DAT). The weed control rating scale was as follows.

0% = no weed control
100% = 100% weed control

The observed percent weed control is set forth in Table 3, which follows. In the table, column 2 gives the application rate in kg./ha.; column 3, the percent weed control of all weeds; column 4 the percent control of grasses; and columns 5 through 11, the percent control of the indicated weeds at the indicated days after treatment (DAT).

The weeds were identified by letters of the alphabet, as follows:

A—Pigweed
B—Morningglory
C—Purslane
D—Black Nightshade
E—Lookingglass

TABLE 3

| | | PERCENT WEED CONTROL | | | | | | | | |
|---|---|---|---|---|---|---|---|---|---|---|
| | | All Weeds | Grasses | A | B | | C | | D | E |
| Compound | kg./ha. | 22 DAT | 79 DAT | 79 DAT | 79 DAT | 233 DAT | 79 DAT | 233 DAT | 79 DAT | 79 DAT |
| 1 | 1.12 | 100 | 100 | 100 | 100 | 0 | 100 | 0 | 100 | 100 |
| | 2.24 | 96 | 100 | 100 | 100 | 97 | 100 | 97 | 100 | 100 |
| | 4.48 | 100 | 67 | 100 | 97 | 100 | 100 | 100 | 100 | 100 |
| Control | 0 | 0 | 0 | 0 | 0 | 0 | 0 | 0 | 0 | 0 |

TRIAL 3

The efficacy of Compound 1 in controlling unwanted vegetation when applied as a directed spray to grapefruit trees established one year in the orchard was determined in the following manner.

Grapefruit trees, variety Star Ruby, were planted one tree per plot in plots measuring about 1.5 meters by 1.8 meters. The trees were about one year old and about 90 cm. tall. The randomized block experimental design was followed, with three replicates per test. The soil was a sandy loam having an estimated organic content of about 0.8 percent. The land where the test was carried out was flat, the soil having small clods. The soil surface was dry and the soil moisture condition was dry. The source of water in this test area was by flood irrigation.

The test compound was formulated in the same manner as described in Trial 2, supra, and then diluted with water to give the correct concentration for application at the desired rate per hectare. The formulations were applied using a $CO_2$ hand-held sprayer, the operator directing the spray to the base of the crop, avoiding the foliage of the crop. The formulation was applied at the rate of 467 l./ha. The experiment was flood irrigated 12 days after treatment.

The trees were observed for possible crop injury beginning 29 days after treatment. The crop injury observed was chlorosis in the leaves. The crop injury rating scale was the same as used in Trial 2. The efficacy of the test compound in controlling weeds and grass around the grapefruit trees was also observed and the weed control rating scale was the same as that used in Trial 2 and described above.

The results are set forth in Table 4, which follows. In the table, column 2 gives the application rate in kg./ha., columns 3, 4, and 5 give the percent crop injury at the indicated days after treatment (DAT); and columns 6 through 10 give the percent weed control at the indicated DAT. The weeds are identified as follows:
A—Pigweed
B—Large Crabgrass
C—Purslane orange trees were treated with directed spray applications of the test compound.

Trees of the Valencia variety of sweet orange were planted in plots measuring about 0.9×0.9 meters, in rows 7.6 meters apart. The trees were about 1 year old and measured about 45 to 60 cm. tall. The trees were planted in sandy soil containing about 1.6 percent organic content, as shown by testing. The experiment was conducted on flat land, the soil containing no clods, and the soil was dry at 1.25 cm. below the surface. The experimental area was sprinkler irrigated, when necessary.

The test compound was formulated as a 25 percent wettable powder which was then diluted with water to provide the application rates desired, as described in the previous trails. The test material was applied using a $CO_2$ backpack sprayer, and the material was applied at the rate of 374 l./ha., as a directed spray to the base of the crop, avoiding the foliage of the crop. Beginning about 25 days after treatment (DAT), the trees were examined for any possible injury caused by the test compound. The crop injury was rated in the same manner as described in Trials 2 and 3 above.

The results are set forth in Table 5, which follows. In the table, column 2 gives the application rate in kg./ha.; and columns 3 through 7 list the percent crop injury at the indicated DAT.

TABLE 5

| | | Percent Crop Injury | | | | |
|---|---|---|---|---|---|---|
| Compound | kg./ha. | 25 DAT | 81 DAT | 119 DAT | 232 DAT | 508 DAT |
| 1 | 1.12 | 10 | 10 | 3 | 0 | 0 |
| | 2.24 | 13 | 13 | 13 | 13 | 27 |
| | 4.48 | 10 | 10 | 10 | 37 | 3 |
| Control | 0 | 0 | 0 | 0 | 0 | 0 |

The efficacy of the test compound in controlling perennial grasses and weeds was also determined and the results are set forth in Table 6, which follows. The weed control rating scale was the same as that used in Trials 2 and 3, set forth above. In the table, column 2 gives the application rate in kg/ha.; columns 3 through 13, the percent weed control of the various weeds and

TABLE 4

| | | % Crop Injury | | | Percent Weed Control | | | | |
|---|---|---|---|---|---|---|---|---|---|
| | | | | | A | | | B | C |
| Compound | kg./ha. | 29 DAT | 126 DAT | 188 DAT | 29 DAT | 126 DAT | 188 DAT | 29 DAT | 29 DAT |
| 1 | 1.12 | 7 | 0 | 0 | 100 | 100 | 98 | 100 | 100 |
| | 2.25 | 10 | 0 | 2 | 100 | 100 | 100 | 100 | 100 |
| | 4.5 | 17 | 3 | 2 | 100 | 100 | 97 | 100 | 100 |
| Control | 0 | 0 | 0 | 0 | 0 | 0 | 0 | 0 | 0 |

TRIAL 4

Another test was run to determine the herbicidal efficacy and crop tolerance to Compound 1 when grasses at the indicated days after treatment (DAT). The weeds and grasses are identified as follows:

A—Pigweed
B—Large Crabgrass
C—Foxtail
D—Sida
E—Bahia Grass

TABLE 6

| | | PERCENT WEED CONTROL | | | | | | | | | |
|---|---|---|---|---|---|---|---|---|---|---|---|
| | | A | | | B | C | | | D | | E |
| Compound | kg./ha. | 25 DAT | 81 DAT | 119 DAT | 232 DAT | 25 DAT | 81 DAT | 119 DAT | 25 DAT | 81 DAT | 119 DAT | 508 DAT |
| 1 | 1.12 | 100 | 100 | 98 | 90 | 99 | 99 | 100 | 100 | 100 | 100 | 73 |
| | 2.24 | 100 | 100 | 100 | 63 | 100 | 100 | 100 | 100 | 100 | 100 | 73 |
| | 4.48 | 100 | 100 | 100 | 100 | 100 | 100 | 98 | 100 | 100 | 100 | 80 |
| Control | 0 | 0 | 0 | 0 | 0 | 0 | 0 | 0 | 0 | 0 | 0 | 0 |

TRIAL 5

A test to determine the herbicidal efficacy and crop tolerance when Compound 1 was soil surface applied as a directed spray to established citrus seedlings was conducted in the following manner.

Sweet orange trees, variety Clemenules, were planted one tree per plot, each plot measuring about 1.25 by 1.25 meters, the plots being in rows 2 m. apart. The trees were about 1 year old. The solid was a sandy loam having an estimated 1 percent organic content. The soil was dry at 1 cm. The soil moisture was intermediate, and the water source was sprinkler irrigation. The compound was formulated in the same manner as described in the previous trials and the test formulations were applied using a CO2 backpack sprayer at an application rate of 240 l./ha.

The results are set forth in Table 7, which follows. In the table, column 2 gives the application rate in kg./ha.; column 3, the crop injury rating; columns 4-6, the percent weed control of all weeds at the indicated days after treatment; and columns 7 through 16, inclusive, the percent control of individual weeds as determined 79 days after treatment (DAT). The injury rating scale is the same as used in the previous trials. The leaf injury observed was that of yellow intervein areas and dry leaf tips.

The weeds are identified by letters of the alphabet, as set forth hereinbelow:

A—Burning Nettle
B—Pigweed
C—Annual Bluegrass
D—Scarlet Pimpernel
E—Knotweed, Prostrate
F—Brassica
G—Lambsquarter
H—Matricaria
J—Wallrocket, Stinking
K—Henbit

TRIAL 6

Another test was run to determine the herbicidal efficacy and crop tolerance of Compound 1, when the compound, formulated as an 80 percent wettable powder (80WP), was surface applied to the soil surrounding young, bearing orange trees during a winter rainy season.

Trees of the Valencia variety of sweet orange were planted in plots measuring about 4×25 meters, with four trees per plot. The trees, about 2 years old, were planted in what is termed a bedded culture. The trial was run on flat land, the soil being clod-free. The soil surface was moist and the soil moisture was moderate at the time the test compound was applied. The randomized block experimental design was followed, using three replicates per test.

The test compound was formulated as an 80% wettable powder, which was diluted with water to provide the application rates desired for use. The test material was applied using a hand-held sprayer, and the material was applied at the rate of 327 liters per hectare to the soil surface in a band width of about 2 meters. The plot area had been sprayed two days before treatment with 1,1'-dimethyl-4,4'-bipyridylium ion, also known as Paraquat, to kill existing weeds. About 78 days after treatment (DAT) with the test compound, the plots were examined to determine the weed control accomplished.

The results are set forth in Table 8, which follows. In the table, column 2 gives the application rate in kg//ha.; columns 3 through 6 list the percent individual weed control observed 78 DAT; and column 7, the percent crop injury 189 DAT.

The weeds are identified as follows:
A—Henbit
B—Shepherdspurse
C—Rockpurslane
D—Chickweed

TABLE 8

| | | Percent Control Individual Weeds 78 DAT | | | | % Crop Injury |
|---|---|---|---|---|---|---|
| Compound | kg./ha. | A | B | C | D | 189 DAT |
| 1 | 0.84 | 100 | 100 | 100 | 100 | 0 |
| | 1 | 100 | 100 | 100 | 100 | 0 |

TABLE 7

| Compound | kg. /ha. | % Crop Injury 132 DAT | Percent Control of All Weeds | | | Percent Individual Weed Control 79 DAT | | | | | | | | | |
|---|---|---|---|---|---|---|---|---|---|---|---|---|---|---|---|
| | | | 34 DAT | 132 DAT | 259 DAT | A | B | C | D | E | F | G | H | J | K |
| 1 | 1.12 | 0 | 72 | 100 | 100 | 100 | 100 | 100 | 100 | 100 | 100 | 100 | 100 | 100 | 100 |
| | 2.24 | 3 | 100 | 100 | 97 | 68 | 100 | 100 | 100 | 100 | 100 | 100 | 100 | 100 | 100 |
| | 4.48 | 2 | 100 | 100 | 98 | 100 | 100 | 100 | 100 | 100 | 100 | 100 | 100 | 100 | 100 |
| Control | 0 | 0 | 0 | 0 | 0 | 0 | 0 | 0 | 0 | 0 | 0 | 0 | 0 | 0 | 0 |

TABLE 8-continued

| Compound | kg./ha. | Percent Control Individual Weeds 78 DAT | | | | % Crop Injury 189 DAT |
|---|---|---|---|---|---|---|
| | | A | B | C | D | |
| | 1.5 | 100 | 100 | 100 | 100 | 0 |
| | 2 | 100 | 100 | 100 | 100 | 0 |
| | 3 | 100 | 100 | 100 | 100 | 0 |
| Control | 0 | 0 | 0 | 0 | 0 | 0 |

In view of its demonstrated herbicidal activity, the novel compound of this invention was also included in a field trial to study the control of the growth of undesired vegetation in a sugarcane field.

TRIAL 7

Stalks of sugarcane, approximately 1½ inches in diameter, were cut from a commercial cane field at midseason, a time when the cane was not yet mature. The stalks were then cut into seed pieces approximately two feet long. The seed pieces were hand planted with 50 percent overlap in planting furrows in prepared beds, and covered with about two inches of soil. The test field was divided into beds and the beds numbered, following a randomized block design. Test materials were applied as aqueous sprays on the same day as the sugarcane was planted. Prior to planting the sugarcane, the beds were seeded with the following weeds, by broadcast application, followed by working of the seeds into the soil: browntop millet (*Panicum fasciculatum*); velvetleaf (*Abutilon theophrasti*); sesbania (*Sesbania exaltata*); pigweed (*Amaranthus sp.*); and jimsonweed (*Datura stramonium*). Also during the preplanting preparation, the soil was treated with commercial materials to control nematodes, soil diseases, insects, and cane diseases.

The test compound was formulated as an 80% wettable powder, which was then diluted with water to yield compositions of suitable concentrations for the desired soil surface application rates.

Three replicates of each treatment and control were run. Observations of both weed control and any possible injury to the sugarcane were made and recorded 2½ weeks and 5 weeks, respectively, after treatment. In this trial a weed control rating of 0–10, wherein 0=no control and 10=100 percent control, was adopted. A crop injury rating of 0-10 was adopted, as follows:

0=no injury
1-3=slight injury
4-6=moderate injury
7-9=severe injury
10=death

The symptoms of crop injury evaluated were chlorotic leaves.

The results of the test are recorded in Table 9, which follows. In the table, column 2 gives the rate in terms of kilogram per hectare (kg./ha.) at which the compound was applied to the soil surface; columns 3 through 12, the weed control ratings of the respective series of weed; and column 13, the crop injury ratings. Purslane (*Portulaca oleracea*) (column 12) was a volunteer growth, and the control thereof was observed and recorded only once, at 5 weeks post-planting and treatment of the sugarcane beds.

TABLE 9

| | | Weed Control Ratings | | | | | | | | | | Crop Injury |
|---|---|---|---|---|---|---|---|---|---|---|---|---|
| | Appln. | Browntop Millet | | Velvetleaf | | Sesbania | | Pigweed | | Jimsonweed | Purslane | |
| Cpd. | Rate kg./ha. | 2½ wks. | 5 wks. | 2½ wks. | 5 wks. | 2½ wks. | 5 wks. | 2½ wks. | 5 wks. | 2½ wks. | 2½ wks. | Ratings 5 wks. |
| 1 | 0.56 | 8.3 | 2 | 10 | 0 | 9.3 | 2.7 | 9.9 | 1.7 | 10 | 3 | 0 |
| | 1.12 | 10 | 6.3 | 10 | 0 | 9.9 | 9.2 | 10 | 8.3 | 10 | 8 | 0 |
| | 2.24 | 10 | 9 | 10 | 3.3 | 10 | 10 | 10 | 9.7 | 10 | 9 | 0 |
| | 4.48 | 10 | 10 | 10 | 1.7 | 10 | 10 | 10 | 10 | 10 | 10 | 0 |
| Control | 0 | 0 | 0 | 0 | 0 | 0 | 0 | 0 | 0 | 0 | 0 | 0 |

The test results set forth above demonstrate the broad spectrum of the herbicidal activity of the instant compound as well as its herbicidal selectivity towards citrus trees and sugarcane.

We claim:

1. 1-[5-(2-Chloro-1,1-dimethylethyl)-1,3,4-thiadiazol-2-yl]-1,3-dimethylurea, having the formula

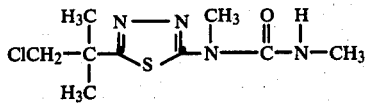

2. A herbicidal composition comprising an inert carrier in admixture with a herbicidal proportion of the compound of claim 1.

3. A method of controlling undesired vegetation which comprises applying to the locus of the undesired vegetation a herbicidally-effective amount of the compound of claim 1.

* * * * *